(12) United States Patent
Melsheimer

(10) Patent No.: US 9,623,206 B2
(45) Date of Patent: Apr. 18, 2017

(54) CATHETER HAVING A SELECTIVELY VARIABLE DEGREE OF FLEXIBILITY

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1357 days.

(21) Appl. No.: 13/460,231

(22) Filed: Apr. 30, 2012

(65) Prior Publication Data

US 2012/0277729 A1  Nov. 1, 2012

Related U.S. Application Data

(60) Provisional application No. 61/480,925, filed on Apr. 29, 2011.

(51) Int. Cl.
*A61M 25/00* (2006.01)
*A61B 17/34* (2006.01)
*A61M 25/01* (2006.01)

(52) U.S. Cl.
CPC ....... *A61M 25/005* (2013.01); *A61B 17/3439* (2013.01); *A61M 25/0012* (2013.01); *A61M 25/0051* (2013.01); *A61M 25/0052* (2013.01); *A61M 25/0053* (2013.01); *A61M 25/0054* (2013.01); *A61M 25/01* (2013.01); *A61M 25/0097* (2013.01); *A61M 2025/0004* (2013.01); *A61M 2025/0006* (2013.01); *A61M 2025/0024* (2013.01); *A61M 2025/0025* (2013.01); *A61M 2025/0059* (2013.01);
(Continued)

(58) Field of Classification Search
CPC ...... A61B 17/3439; A61M 2015/0172; A61M 2015/0062; A61M 2015/0063; A61M 2015/0059; A61M 2015/0024; A61M 2015/0025; A61M 2015/0004; A61M 2015/0006; A61M 25/0012; A61M 25/005; A61M 25/0051; A61M 25/0052; A61M 25/0053; A61M 25/0054
See application file for complete search history.

(56) References Cited

U.S. PATENT DOCUMENTS 5,460,170 A * 10/1995 Hammerslag ...... A61B 17/3439
                                              600/201
6,165,163 A * 12/2000 Chien ............... A61M 25/0053
                                              604/523
(Continued)

*Primary Examiner* — Laura Bouchelle
*Assistant Examiner* — Anh Bui
(74) *Attorney, Agent, or Firm* — Brinks Gilson & Lione

(57) ABSTRACT

A catheter having a selectively variable degree of flexibility includes an elongate tubular outer member and an elongate tubular inner member disposed within the outer member. The catheter further includes a cavity disposed in between the outer and inner members. A tubular braid of filaments may be disposed within the cavity. The outer and inner members are movable relative to each other along intermediate portions thereof when in a first configuration, and are not movable relative to each other when in a second configuration. When the inner and outer members are in the first configuration, the tubular braid of filaments is movably disposed relative to at least one of the outer member and the inner member. When the inner and outer members are in the second configuration, the inner and outer members clamp the tubular braid of filaments in a fixed position relative to the inner and outer members.

27 Claims, 4 Drawing Sheets

(52) U.S. Cl.
CPC ............ *A61M 2025/0062* (2013.01); *A61M 2025/0063* (2013.01); *A61M 2025/0175* (2013.01)

(56) References Cited

U.S. PATENT DOCUMENTS

| | | | | |
|---|---|---|---|---|
| 6,228,068 | B1* | 5/2001 | Yoon | A61B 17/3439 604/105 |
| 9,265,526 | B1* | 2/2016 | Abdou | A61B 17/3439 |
| 2002/0035347 | A1* | 3/2002 | Bagaoisan | A61M 25/1011 604/35 |
| 2003/0191451 | A1* | 10/2003 | Gilmartin | A61M 25/005 604/527 |
| 2004/0116897 | A1* | 6/2004 | Aboul-Hosn | A61B 17/3421 604/508 |
| 2009/0240202 | A1* | 9/2009 | Drasler et al. | 604/164.03 |
| 2012/0157971 | A1* | 6/2012 | Herrig | A61M 1/3653 604/527 |

* cited by examiner

CATHETER HAVING A SELECTIVELY VARIABLE DEGREE OF FLEXIBILITY

RELATED APPLICATION

This application claims the benefit of U.S. Provisional Application No. 61/480,925, filed Apr. 29, 2011, which is incorporated herein by reference in its entirety.

TECHNICAL FIELD

The present disclosure relates generally to medical devices, and more particularly to a catheter having a selectively variable degree of flexibility.

BACKGROUND

Catheters may be used in percutaneous intervention procedures to deliver a medical device to a treatment site within a patient. For a given procedure, the type of catheter may be selected based on the catheter's profile, steerability, lubricity, tip characteristics, length, rigidity, and/or flexibility. The flexibility of the catheter that is selected may be suitable for the catheter to be navigated through bodily passageways of the patient to the treatment site, but may not be suitable for delivery of a medical device through the catheter to the treatment site. For example, the flexibility of the catheter that is suitable for navigating the catheter to the treatment site may be too flexible for being suitable for delivery of the medical device through the catheter to the treatment site. Alternatively, the rigidity or stiffness of the catheter that is suitable for delivery of the medical device through the catheter to the treatment site may be too rigid or stiff for the catheter to be navigated through the vasculature of the patient to the treatment site.

BRIEF SUMMARY

A catheter includes an elongate tubular outer member; an elongate tubular inner member disposed within the outer member; an annular cavity disposed in between the outer member and the inner member; and a tubular braid of filaments disposed in the annular cavity; wherein the outer member and the inner member are movable relative to each other along intermediate portions thereof when in a first configuration and are not movable relative to each other when in a second configuration; wherein the tubular braid of filaments is movably disposed relative to at least one of the outer member and the inner member when the outer member and the inner member are in the first configuration; and wherein the tubular braid of filaments is fixedly disposed relative to both the outer member and the inner member when the outer member and the inner member are in the second configuration. The catheter further includes a means for fixedly disposing the tubular braid of filaments relative to both the inner member and the outer member when the inner member and the outer member are in the second configuration. The means for fixedly disposing the tubular braid of filaments comprises a vacuum source for applying a vacuum to the cavity sufficient to cause the tubular braid of filaments to frictionally engage both the inner and outer member. The catheter further comprises a port operably connected to the cavity for applying the vacuum.

A medical system includes a catheter and a vacuum source. The catheter comprises an elongate tubular outer member; an elongate tubular inner member disposed within the outer member; an annular cavity disposed in between the outer member and the inner member; and a tubular braid of filaments disposed in the annular cavity. The tubular braid of filaments is at least partially movable relative to at least one of the inner member and the outer member. The vacuum source is in communication with the annular cavity, and is configured to apply a vacuum to the annular cavity to prevent movement between the tubular braid of filaments and both the inner member and the outer member.

A method of selectively varying flexibility of a catheter includes navigating a proximal end of the catheter to a treatment site within a patient; clamping a tubular braid of filaments between an elongate tubular outer member of the catheter and an elongate tubular inner member of the catheter, the inner member being disposed within the outer member, and the tubular braid of filaments being disposed in an annular cavity in between the outer member and the inner member; and delivering a medical device through a lumen of the catheter to the treatment site.

DETAILED DESCRIPTION

Figure 1:
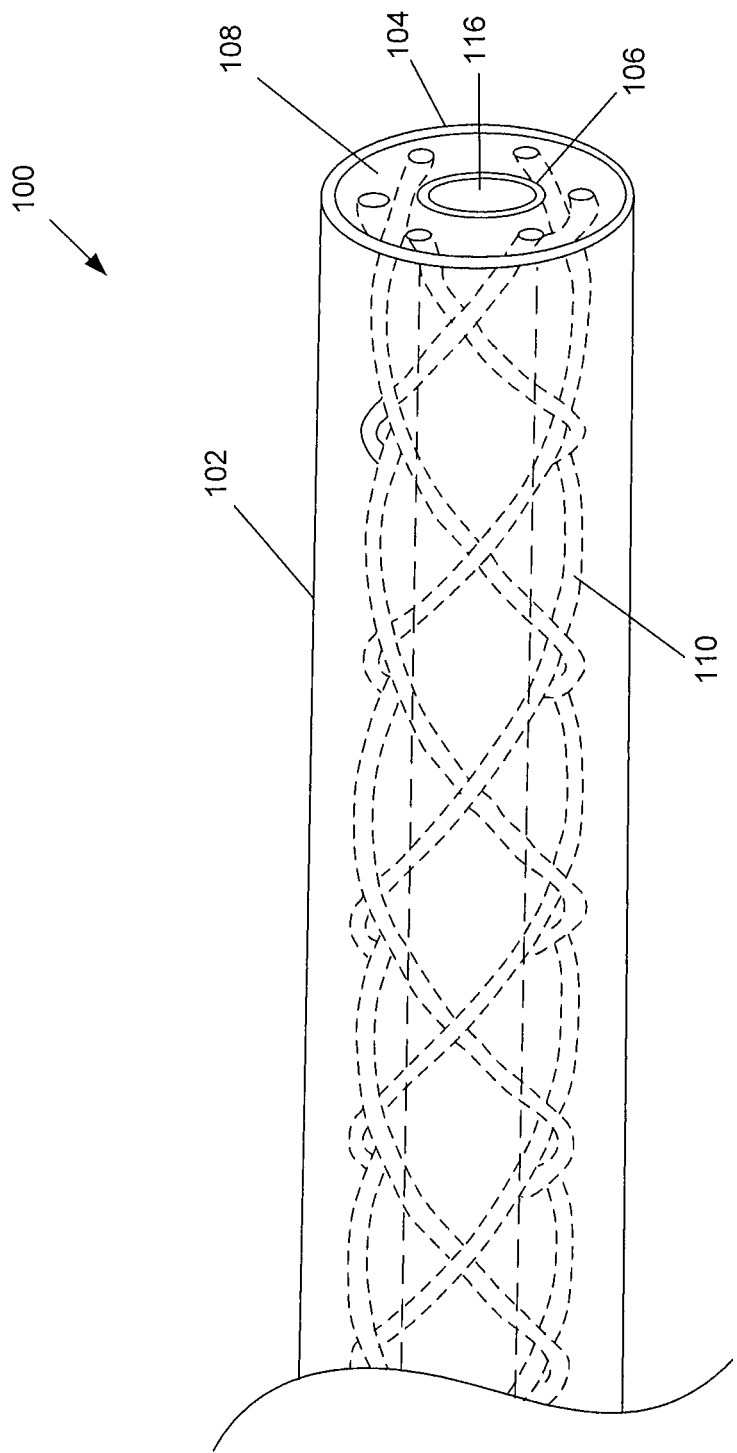
FIG. 1 shows a side view, partially in cross-section, of at least a part of a tubular portion of a catheter.

The present disclosure describes a catheter that has a selectively variable degree of flexibility. The flexibility may be selective among two degrees of flexibility, a first degree of flexibility that is suitable for navigation through bodily passages of a patient, such as vessels, ducts, and/or cavities, and a second degree of flexibility that is suitable for delivery and/or removal of a medical device through the catheter. The catheter may include an elongate tubular outer member and an elongate tubular inner member disposed within the outer member. The inner member disposed within the outer member may form an annular cavity in between an inner surface of the outer member and an outer surface of the inner member. A tubular braid of filaments may be disposed within the cavity.

The outer and inner members may be movable relative to each other along intermediate portions thereof when in a first configuration and are not movable relative to each other when in a second configuration. When the inner and outer members are in the first configuration, the tubular braid of filaments is movably disposed relative to at least one of the outer member and the inner member. In addition, when the inner and outer members are in the first configuration, the catheter may have the first degree of flexibility that is suitable for navigation through passageways to and from a treatment site within the patient. When the inner and outer members are in the second configuration, the inner and outer members clamp the tubular braid of filaments in a fixed position relative to the outer member and the inner member, which prevents the filaments of the braid from moving across each other. When the inner and outer members clamp the tubular braid of filaments, the catheter may have the second degree of flexibility that is suitable for delivery or removal of a medical device through a lumen of the catheter.

The outer and inner members may be configured in the second configuration when a vacuum is applied to the cavity. The vacuum may be applied to the cavity by removing all or less than all of the gaseous particles, such as air molecules, from the cavity. The vacuum may be a perfect vacuum in which the cavity is completely devoid of gaseous particles. Alternatively, the vacuum may comprise a partial vacuum in which the cavity comprises some gaseous particles. Whether the vacuum comprises a perfect vacuum or a partial vacuum, the pressure within the cavity is less than the ambient pressure surrounding the catheter. The pressure inside the cavity may be an amount sufficiently less than the ambient pressure such that the outer and inner members may be in the second configuration. The outer and inner members may be configured in the first configuration by removing the vacuum from the cavity. The vacuum may be removed from the cavity by inserting or injecting gaseous particles into the cavity. Alternatively, the vacuum may be removed by allowing gaseous particles from the ambient environment to move into the cavity. When the gaseous particles from the ambient environment move into the cavity, the pressure within the cavity may be equal or substantially equal to the pressure of the ambient environment. Through application and removal of the vacuum to the cavity, the catheter may have varying degrees of flexibility that are suitable for both navigation of the catheter through bodily passages within the patient and navigation of the medical device through the catheter. Application of the vacuum to the cavity to provide varying flexibility of the catheter may be advantageous in that in event that a leak occurs in the cavity, there may be a diminished likelihood that a foreign substance is released into the passage of the body. Also, in the event of a stress failure of the cavity, a leak resulting from the stress failure may not cause trauma associated with a sudden, high-pressure vessel failure.

In an alternative catheter, the flexibility of the catheter may be varied from a first flexibility that is suitable for navigation through bodily passages within the patient to a second flexibility that is suitable for delivery of a medical device to the treatment site by applying pressure rather than a vacuum to an annular cavity. The annular cavity may be formed in between either the outer member or the inner member and an elongate tubular middle member disposed in between the outer member and the inner member. The middle member may form two annular cavities—a first cavity in between the outer member and the middle member, and a second cavity in between the inner member and the middle member. The tubular braid may be disposed in the first annular cavity or the second annular cavity. Pressure may be applied, such as by inserting or injecting a gas or liquid, to the annular cavity in which the tubular braid is not disposed. For example, where the braid is disposed in the first annular cavity, pressure may be applied to the second annular cavity. Application of pressure to the second annular cavity may exert a radially outward force on the middle member, causing the middle member to move toward the outer member and clamp the tubular braid in between the outer member and the inner member in an immobile or fixed position relative to both the outer member and the inner member. Similarly, where the braid is disposed in the second annular cavity, pressure may be applied to the first annular cavity. Application of the pressure to the first annular cavity may exert a radially inward force on the middle member, causing the middle member to move toward the inner member and clamp the tubular braid in between the middle member and the inner member an immobile or fixed position relative to the middle member and the inner member. The alternative catheter having a middle member may have an increased cross-sectional area, may have an increased stiffness in an unbiased state (i.e., the state of the catheter when pressure is not being applied to the catheter), and/or may be more expensive to manufacture as compared to the catheter that does not have the middle member.

FIG. 1 shows a side view, partially in cross-section, of at least a part of a tubular portion 102 of a catheter 100. The part of the tubular portion 102 shown in FIG. 1 may be representative of the entire tubular portion 102, extending a length of the tubular portion 102 from a proximal end to a distal end of the tubular portion 102. Alternatively, the part of the tubular portion 102 shown in FIG. 1 may be representative of a portion that is less than the entire tubular portion 102. The tubular portion 102 may include an elongate tubular outer member 104, and an elongate tubular inner member 106 disposed within the outer member 104. The tubular inner portion 106 may comprise a central lumen 116 longitudinally disposed therethrough and extending from a proximal end of the inner member 104 to a distal end of the inner member 104. In one example, the central lumen 116 may comprise a single lumen. In an alternative example, the central lumen 116 may comprise multiple lumens. The central lumen 116 may be configured to deliver one or more medical devices to a treatment site within a patient. An annular cavity 108 may be disposed in between the outer member 104 and the inner member 106. A tubular braid of filaments 110 may be disposed in the annular cavity 108.

Figure 2A:
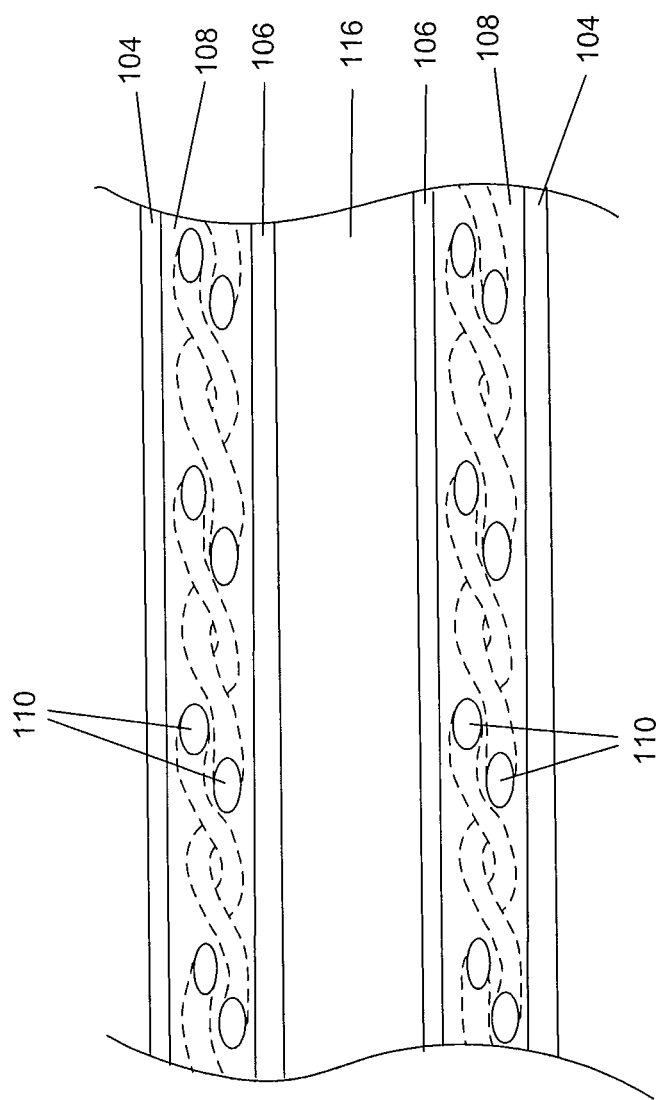
FIG. 2A shows a cross-sectional side view of at least a part of the tubular portion of the catheter of FIG. 1, illustrating an outer member and an inner member of the catheter in a first configuration, and a tubular braid of filaments movably disposed in a cavity in between the outer member and the inner member.

The outer member 104 and the inner member 106 may be configured in a first configuration and a second configuration. FIG. 2A shows a cross-sectional side view of the tubular portion 102 of the catheter 100, illustrating the outer member 104 and an inner member 106 in the first configuration. The first configuration may be an unbiased configuration. The first configuration may be an unbiased configuration because the pressure within the cavity 108 may be equal or substantially equal to the pressure of the ambient environment surrounding the catheter 100. When the outer member 104 and the inner member 106 are in the first configuration, the tubular braid of filaments 110 may be movably disposed within the cavity 108. A thickness of the cavity 108, which may be a distance from an inner wall of the outer member 104 to an inner wall of the inner member 106, may be greater than a thickness of the tubular braid of filaments 110. The thickness of the tubular braid of filaments 110 may be determined based on a diameter of one or more of the filaments of the tubular braid of filaments 110. When the outer member 104 and the inner member 106 are in the first configuration, the cavity 108 may comprise a gas, such as air, oxygen, and/or carbon dioxide. Additionally, when the outer member 104 and the inner member 106 are in the first configuration, the catheter 100 may comprise a degree of flexibility that is suitable for navigation of the catheter 100 through a bodily path, such as a body cavity, duct, or vessel, inside a patient and toward a treatment site within the patient.

Figure 2B:
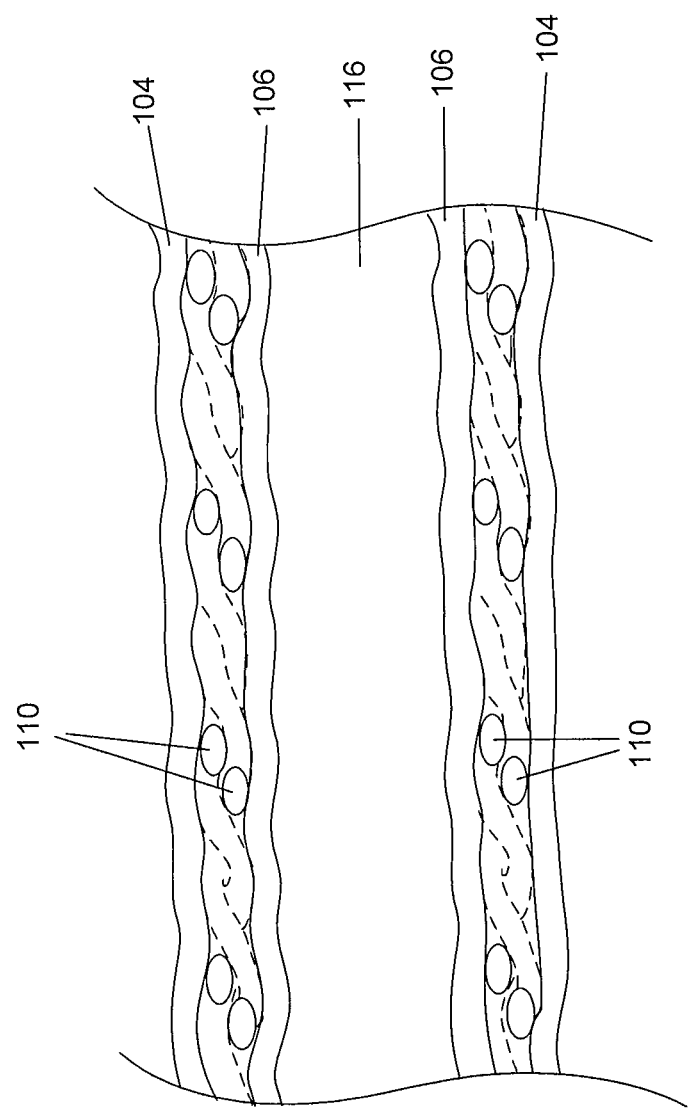
FIG. 2B shows a cross-sectional side view of at least a part of the tubular portion of the catheter of FIG. 1, illustrating the inner member and the outer member of the catheter in a second configuration, and the tubular braid of filaments fixedly disposed in between the outer member and the inner member.

FIG. 2B shows a cross-sectional side view of the tubular portion 102 of the catheter 100, illustrating the outer member 104 and the inner member 106 of the tubular portion 102 in the second configuration. The second configuration may be a biased configuration. The second configuration may be a biased configuration because the pressure within the cavity 108 is less than the pressure of the ambient environment surrounding the catheter 100. When the outer member 104 and the inner member 106 are in the second configuration, the tubular braid of filaments 110 may be fixedly disposed in the cavity 108 relative to both the outer member 104 and the inner member 106. The outer member 104 and the inner member 106 may bias or clamp the tubular braid of filaments 110 in the fixed position relative to the outer and inner members 104, 106. Clamping the tubular braid of filaments may prevent the filaments from moving across one another, which may immobilize or lock the catheter 100 in the position or configuration in which the catheter 100 is disposed when the tubular braid 110 is clamped. The thickness of the cavity 108 when the outer and inner members 104, 106 are in the second configuration may be less than the thickness of the cavity 108 when the outer and inner members 104, 106 are in the first configuration. When the outer member 104 and the inner member 106 are in the second configuration, the cavity 108 may comprise a vacuum. When the cavity 108 comprises a vacuum, the inner wall of the outer member 104 and the outer wall of the inner member 106 may be drawn toward each other, which compresses the cavity 108 and clamps the tubular braid of filaments 110 in the fixed position relative to the outer and inner members 104, 106. Additionally, when the outer member 104 and the inner member 106 are in the second configuration, the catheter 100 may comprise a degree of flexibility that is greater than the degree of flexibility that the catheter 100 comprises when the outer and inner members 104, 106 are in the first configuration.

The outer member 104 and the inner member 106 may be configured in the first configuration and the second configuration by application and/or removal of the vacuum to the cavity 108. For example, when the outer member 104 and the inner member 106 are in the first configuration, the cavity may comprise a gas, such as air, oxygen, and/or carbon dioxide. In the first configuration, the outer and inner members 104, 106 may be unbiased and the outer member 104 and the inner member 106 are movable relative to each other along intermediate portions thereof. The tubular braid of filaments 110 may be movably disposed within the cavity 108. When the vacuum is applied to the cavity 108, the gas may be withdrawn from the cavity 108, and the inner walls of the outer and inner members 104, 106 may be biased and moved toward each other into the second configuration. In the second configuration, the outer and inner members 104, 106 may not be movable relative to each other. In addition, the outer and inner members 104, 106 clamp the tubular braid of filaments into a fixed position relative to the outer and inner members 104, 106. When the vacuum is removed from the cavity 108, the gas may pass into the cavity, and the first and second members 104, 106 may be in the first configuration and move into an unbiased state.

Figure 3:
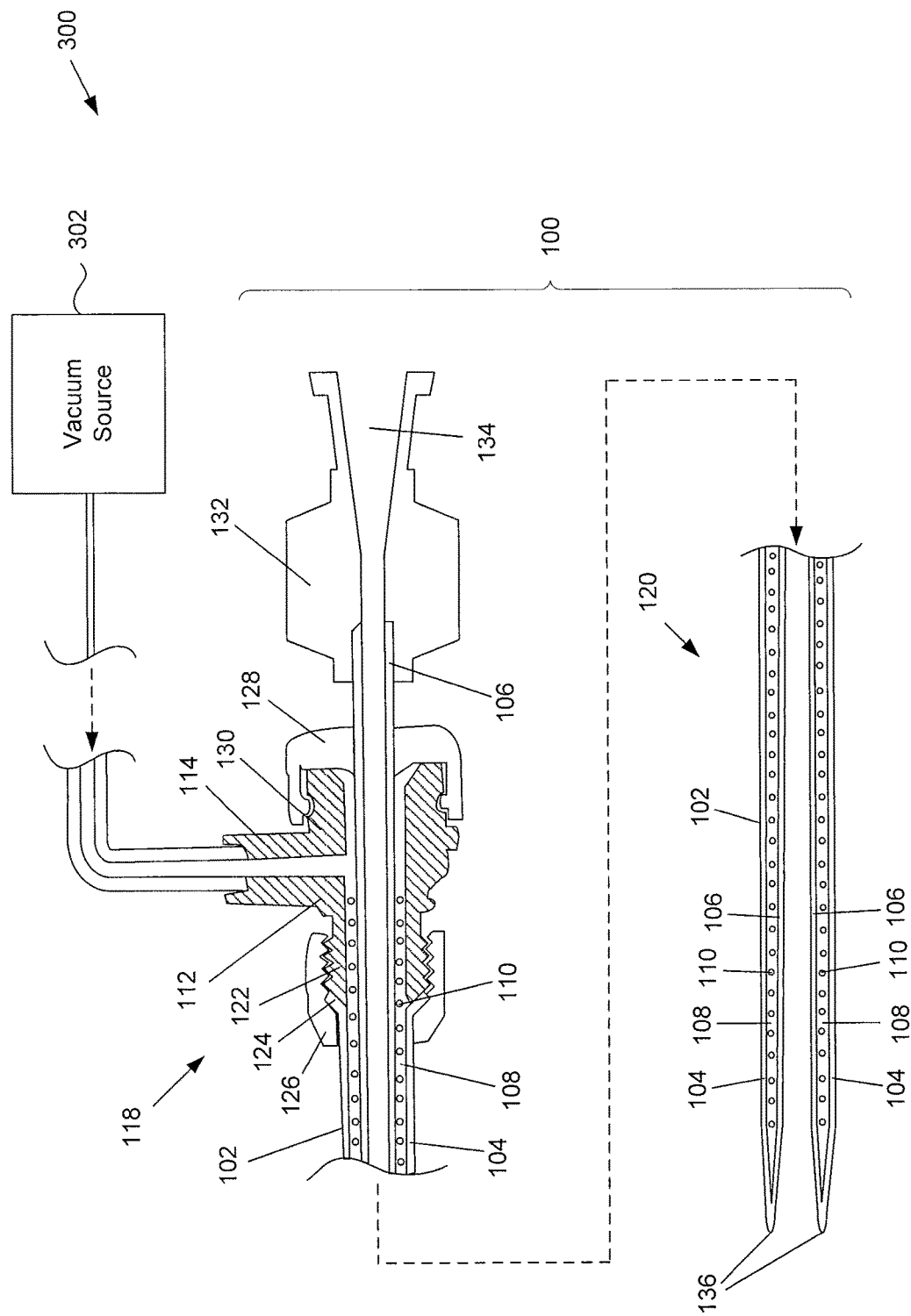
FIG. 3 shows a medical system that includes the catheter of FIG. 1 connected to a vacuum source, illustrating a cross-sectional side view of proximal and distal portions of the catheter, where the vacuum source is connected to the proximal portion.

FIG. 3 shows a medical system 300 that includes the catheter 100 shown in cross-section connected to a vacuum source 302. In particular, FIG. 3 shows the vacuum source 302 connected to a proximal portion 118 of the catheter 100. The vacuum source 302 of the medical system 300 may be operably connected to the annular cavity 108. The vacuum source 302 may be configured to apply the vacuum to and/or remove the vacuum from the annular cavity 108. For example, the vacuum source 302 may be configured to apply the vacuum to the cavity 108 by removing the gas from the cavity 108. Similarly, the vacuum source 302 may be configured to remove the vacuum from the cavity 108 by inserting the gas into the cavity 108. In one example, the vacuum source 202 comprises a syringe. Other vacuum sources may be used.

The vacuum may be applied to and/or removed from the cavity 108 through a port of the catheter 100. The port may be in fluid communication with and/or operably connected to the cavity 108 and may be configured to allow the gas to pass therethrough and into and/or out of the cavity 108. An example port is shown in FIG. 3. The example port shown in FIG. 3 comprises a side arm 114 of a hub 112. The hub 112 may be connected to a proximal end of the outer member 104 and/or the inner member 106. The hub 112 may be used to navigate a distal end of the catheter 100 to the treatment site within the patient, to insert one or more medical devices into the tubular portion 102 of the catheter 100 for delivery to the treatment site, and/or to apply the vacuum to and/or remove the vacuum from the cavity 108. The vacuum source 302 may be in fluid communication with the annular cavity 108 by being connected to the side arm 114. The vacuum source 302 may be configured to apply the vacuum to and/or remove the vacuum from the annular cavity 108 by passing the gas through the side arm 114. For example, the vacuum source 302 may be configured to apply the vacuum to the cavity 108 by removing the gas from the cavity 108 through the side arm 114. Similarly, the vacuum source 302 may be configured to remove the vacuum from the cavity 108 by inserting the gas into the cavity 108 through the side arm 114. In an alternative example, the vacuum may be removed from the cavity 108 by disconnecting the vacuum source 302 from the side arm 114, allowing gas, such as air in the surrounding environment, to pass through the side arm 114 and enter the cavity 108.

In an alternative catheter, the catheter may comprise a second port operably connected to the cavity 108. The second port may be disposed at a location of the catheter that is different from the side arm 114. For example, the second port may comprise a second side arm of the hub. Alternatively, the second port may be disposed on the tubular portion 102, such as on an outer surface of the outer member 104. The second port may be configured to be sealed and unsealed. In one example, the second port may be sealed by affixing a cap to the port and may be unsealed by removing the cap from the port. When the vacuum is applied to the cavity 108, the second port may be sealed, for example by affixing a cap to the second port. Rather than disconnect the vacuum source from the side port 114, the cap affixed to the second port may be removed, allowing gas, such as air in the surrounding environment, to pass through the second port and enter the cavity 108. Alternatively or in addition, the vacuum source 302, the second port, and the side arm 114 may be connected to a three-way stop-cock. The stop-cock may be configured to be alternatingly in a first position and a second position. In the first position, the stop cock may be configured to allow the vacuum to be applied to the cavity 108, such as by allowing the vacuum source 302 to apply a suction to cavity 108 and remove the gas from the cavity 108. In the second position, the stop cock may be configured to allow the vacuum to be removed from the cavity 108, such as by allowing air from the ambient surroundings to pass through the second port and into the cavity 108.

Before the vacuum source 302 applies the vacuum to the cavity 108, the outer member 104 and the inner member 106 may be in the first configuration, where the outer member 104 and the inner member 106 may be movable relative to each other. Also, in the first configuration, the tubular braid of filaments 110 may be movably disposed within the cavity 108 relative to at least one of the outer member 104 and the inner member 106. When the vacuum source 302 applies the vacuum to the cavity 108, the outer member 104 and the inner member 106 may be configured in the second configuration and clamp the tubular braid of filaments 110 in a fixed position relative to the outer member 104 and the inner member 106. When the vacuum is removed from the cavity 108, the outer and inner members 104, 106 may be configured in the first configuration, where the outer and inner members 104, 106 are movable relative to each other, and the tubular braid of filaments 110 may be movably disposed in the cavity 108 relative to the outer and inner member 104, 106.

The tubular braid of filaments 110 longitudinally extends in the cavity 108 over at least a portion of the inner member 106. In one example, the tubular braid of filaments 110 extends in the cavity 108 over the entire length of the cavity 108, from a proximal end of the cavity 108 to a distal end of the cavity 108. In another example, the tubular braid of filaments 110 longitudinally extends in the cavity 108 over a portion of the inner member 106 that is less than the entire length of the cavity 108. For example, the tubular braid of filaments 110 may extend from the proximal end of the cavity 108 to a position of the tubular portion 102 that is proximal the distal end of the cavity 108. In another example, the tubular braid of filaments 110 may extend from the distal end of the cavity 108 to a position of the tubular portion 102 that is distal the proximal end of the cavity 108. In another example, the tubular braid of filaments 110 may extend from a position of the tubular portion 102 that is distal the proximal end of the cavity 108 to a position of the tubular portion 102 that is proximal the distal end of the cavity 108.

In an alternative catheter, the catheter may comprise more than one tubular braid of filaments, for example a first tubular braid of filaments and a second braid of filaments. The first tubular braid of filaments may longitudinally extend in the cavity 108 over a first portion of the inner member 106, and the second tubular braid may longitudinally extend in the cavity 108 over a second portion of the inner member 106. Alternatively, the alternative catheter may comprise more than two tubular braids of filaments that longitudinally extend in the cavity 108 over more than two different portions of the inner member 106.

The hub 112 may further include a distal portion 122. The distal portion 122 may be configured to secure connection of the outer member 104 of the tubular portion 102 to the hub 112. In one example, the proximal end of the outer member may comprise a flared end 124. The distal portion 122 may be configured to clamp the flared end 124 of the outer member 104 to the hub 112. In one example, the distal portion 122 comprises a threaded portion. The threaded portion 122 may be configured to engage with a cylindrical cap 126 having a threaded portion disposed on an inner surface of the cap 126. The cap 126 may be disposed over at least one of the outer member 104 of the tubular portion 102 and the threaded distal portion 122 of the hub 112. When the cap 126 is disposed over only the outer member 104, the cap 126 may be slidably disposed over the outer member 104. When the cap 126 is disposed over both the outer member 104 and the distal threaded portion 122 of the hub 112, the inner threaded portion of the cap 126 may be engaged with the threaded portion 122, and the cap may not be slidably disposed over the outer member 104. To connect the outer member 104 to the hub 112, the flared end 124 of the outer member 104 may be abutted against a distal end of the distal portion 122. The cap 126 may be slidably moved in a proximal direction from a position distal the flared end 124 of the outer member 104 to the distal end of the distal portion 122 such that a proximal-most thread of the inner threaded portion of the cap 126 engages with a distal-most thread of the threaded portion 122. When the proximal-most thread of the inner threaded portion of the cap 126 engages with the distal-most thread of the threaded portion 122, the cap 126 may be rotated either clockwise or counterclockwise to be longitudinally moved in a proximal direction. As the cap 126 is being rotated, the cap 126 is moving to a clamped position, in which a distal end of the cap 126 engages with the flared end 124 of the outer member 104 and clamps the distal end of the cap 126 to the distal end of the distal portion 122. In the clamped position, a hermetic seal may be formed in between the outer member 104 and the distal portion 122. The hermetic seal may prevent the vacuum from being removed from the cavity 108 when the vacuum is being applied to and/or maintained on the cavity 108.

Configurations alternative to the threaded configurations of the distal portion 122 of the hub 112 and the cap 126 may be used. For example, the outer member 104 may comprise an elastic material such that when a radially outward bias is applied to an inner wall of the outer member 104, an inner diameter of the proximal end outer member 104 may expand from a first diameter to a second diameter. The first diameter may be smaller than an outer diameter of the distal portion 122. The second diameter may be larger than the outer diameter of the distal portion 122. When the inner diameter of the proximal end of the outer member 104 is moved to the second diameter, the proximal end of the outer member 104 may be moved over the distal portion 122 of the hub 112. When the proximal end of the outer member 104 is moved over the distal portion 122, the radially outward bias may be removed and the inner diameter of the proximal end of the outer member 104 may retract toward the first diameter and be disposed about the outer surface of the distal portion 122. When the proximal end of the outer member 104 is disposed over the distal portion 122, the hermetic seal in between the outer member 104 and the distal portion 122 of the hub 112 may be formed. Alternatively or in addition, a clamp may be positioned over and around the distal portion 122 of the hub 112 and the proximal end of the outer member 104 disposed over the distal portion 122. The clamp may be configured to clamp the inner surface of the outer member 104 to the outer surface of the distal portion 122 and form the hermetic seal.

The hub 112 may further comprise a hermetic seal 128 disposed at a proximal end of the cavity 108. The hermetic seal 128 may be configured to provide an airtight seal at the proximal end of the cavity that prevents leakage of the gas from the proximal end of the cavity 108. In one example, as shown in FIG. 3, the hermetic seal 128 may be connected to a middle portion 130 of the hub 112 and the inner member 106 of the tubular portion 102. The middle portion 130 may comprise a portion of the hub 112 that is proximal the distal portion 122 and proximal the proximal end of the outer member 104. As shown in FIG. 3, the middle portion 130 may include the side arm 114. The hermetic seal 128 may comprise a silicon diaphragm. The silicon diaphragm may be connected to the middle portion 130 and the inner member 106 to form a hermetic seal that prevents gas, such as air, oxygen, and/or carbon dioxide, from exiting the cavity 108 when the vacuum is applied to and/or maintained on the cavity 108.

In an alternative catheter, the hermetic seal 128 may comprise one or more layers of heat shrink material. For example, a first heat shrink layer may be disposed over the inner member 106. In an embodiment where the tubular braid 110 extends to the proximal end of the cavity, a second heat shrink layer may be disposed over the first heat shrink layer and the tubular braid 110. Alternatively, where the tubular braid is not disposed over the inner member 106 at the proximal end of the cavity 108, then the second heat shrink layer may not be used. An outer member, such as the outer member 104 or a tubular member similar in cross-sectional shape and/or composition to the outer member 104, may be disposed over the inner member 106, the first heat shrink layer, the tubular braid, and/or the second heat shrink layer. Heat may be applied to the catheter at the proximal end of the cavity 108 to form the hermetic seal 128. In one example where the tubular braid 110 is disposed in between the first heat shrink and the second heat shrink, the tubular braid 110 may be fixedly attached to the hermetic seal 128.

The hub 112 may further comprise a proximal portion 132. As shown in FIG. 3, the proximal portion 132 may be connected to and disposed about the proximal end of the inner member 106. In one example, the proximal portion 132 may be connected to the proximal end of the inner member 106 by being molded over the proximal end of the inner member 106. The proximal portion 132 may comprise a working channel 134. The working channel 134 may be in communication and establish patency with the central lumen 116 of the tubular portion 102. The medical device that is to be delivered to the treatment site may be inserted into the working channel 134 and into the central lumen 116. Thereafter, the medical device may be distally moved through the central lumen 116 toward the treatment site.

FIG. 3 also shows a distal portion 120 of the catheter 100. The distal portion 120 may comprise a hermetic seal 136 disposed at the distal end of the cavity 108. Similar to the hermetic seal 128 disposed at the proximal end of the cavity 108, the hermetic seal 136 may be configured to provide an airtight seal at the distal end of the cavity 108 that prevents leakage of the gas from the distal end of the cavity 108. In one example, as shown in FIG. 3, the hermetic seal 136 may comprise an annular termination. The annular termination 136 may comprise a connection of the distal end of the outer member 104 and the distal end of the inner member 106. In order to form the termination 136, the distal portion 120 may comprise a taper portion, at which the outer member 104 and the inner member 106 distally converge to form the termination 136. The distal end of the outer member 104 may be connected to the distal end of the inner member 106 at the termination 136 such that gas, such as air, oxygen, and/or carbon dioxide, is prevented from exiting the cavity 108 when the vacuum is applied to and/or maintained on the cavity 108.

Alternatively or in addition, the hermetic seal 136 may comprise one or more layers of heat shrink material. For example, a first heat shrink layer may be disposed over the inner member 106. In an embodiment where the tubular braid 110 extends to the distal end of the cavity 108, a second heat shrink layer may be disposed over the first heat shrink layer and the tubular braid 110. Alternatively, where the tubular braid is not disposed over the inner member 106 at the distal end of the cavity 108, then the second heat shrink layer may not be used. The outer member 104 may be disposed over the inner member 106, the first heat shrink layer, the tubular braid 110, and/or the second heat shrink layer. Heat may be applied to the catheter at the distal end of the cavity 108 to form the hermetic seal 136. In one example where the tubular braid 110 is disposed in between the first heat shrink and the second heat shrink, the tubular braid 110 may be fixedly attached to the hermetic seal 136.

The filaments that comprise the tubular braid of filaments 110 may comprise a polymer material, such as polyamide (e.g., nylon) or elastomer (e.g., polyether block amide), a thermoplastic material, carbon fibers, metallic alloys, stainless steel, aramid fibers, polyethylene, and/or glass fibers. The filaments may comprise other materials. In one example, the tubular braid may comprise a diameter in the range from approximately 0.050 inches to approximately 0.080 inches. For example, the diameter of the tubular braid may be 0.054 inches. In addition, as shown in FIG. 1, the tubular braid of filaments 110 may comprise an orientation that is approximately forty-five degrees from a longitudinal axis of the catheter 100. Other orientations having degrees from the longitudinal axis of the catheter 100 other than forty-five degrees may be used. Also, the tubular braid 110 may comprise three or more filaments or strands. The tubular braid 110 shown in FIG. 1 shows six filaments. However, other amounts of filaments may be determined. For example, the tubular braid may comprise sixteen filaments. In addition, in one example of the tubular braid, the thickness or diameter of the filaments may range from approximately 0.001 inches to 0.002 inches. For example, the diameter of the filaments may be 0.0015 inches. Also, in one example of the tubular braid, the cross-over of the braid may range from approximately forty-five times in a linear inch to ninety times in the linear inch. For example, the filaments may cross over each other sixty times in the linear inch.

Where the hermetic seal 128 and/or the hermetic seal 136 comprises one or more tubular heat shrinks, the catheter 100 may be manufactured by placing the inner member 106 over a mandrel. The inner member 106 may comprise a polymer material. A heat shrink tubing may be positioned over the inner member 106. The heat shrink tubing may comprise a thermoplastic material such as polyolefin, fluoropolymer (such as FEP, PTFE or Kynar), PVC, neoprene, silicone elastomer or Viton. Other heat shrink materials may be used. The heat shrink tubing may be positioned over the entire length of the cavity 108. Alternatively, the heat shrink tubing may be positioned over only one or more portions of the inner member 106, such as at the proximal end and/or the distal end of the cavity 108. The tubular braid of filaments 110 may be positioned over the inner member 106 and the heat shrink tubing. Alternatively, the tubular braid of filaments 110 may be positioned over portions of the inner member 106 at which the heat shrink tubing is not also positioned. For example, a proximal heat shrink tubing may be positioned over the inner member 106 at the proximal end of the cavity 108, a distal heat shrink tubing may be positioned over the inner member 106 at the distal end of the cavity 108, and the tubular braid of filaments 110 may be positioned over a portion of the inner member 106 that is in between the proximal and distal ends of the inner member 106. Alternatively, the tubular braid of filaments 110 may be positioned over only one of the proximal heat shrink tubing and the distal heat shrink tubing.

A second heat shrink tubing may be positioned over the inner member 106 after the tubular braid of filaments 110 is positioned over the inner member 106. If the tubular braid of filaments 110 is positioned over the inner member 106 at portions of the inner member 106 that the first heat shrink tubing is not positioned, then the second heat shrink tubing may not be used. Subsequently, the outer member 104 may be positioned over the inner member 106, the first heat shrink tubing, the tubular braid of filaments 110, and/or the second heat shrink tubing. Heat may be applied to the proximal and distal ends of the inner and outer members 104, 106 to form the hermetic seals at the proximal and distal ends of the inner and outer members 104, 106. The annular cavity 108 may be determined by the outer wall of the inner member 106, inner wall of the outer member 104, and the hermetic seals at the proximal and distal ends of the inner and outer members 104, 106.

The hub 112 may be connected to the proximal end of the tubular portion 102. The hub 112 may be positioned so that ports and/or arms of the hub may establish patency with the cavity 108, the central lumen 116, and/or other lumens that the catheter may have for delivery of medical devices or tools to the treatment site of the patient. For example, the hub 112 may be positioned so that the side arm 114 is in fluid communication with and/or operably connected to the cavity 108.

The catheter 100 and/or the medical system 200 that includes the catheter 100 and the vacuum source 202 may be used in a percutaneous intervention procedure to deliver one or more medical device to a treatment site within a patient. In the percutaneous intervention procedure, the distal end of the catheter 100 may be navigated to the treatment site within a patient. During navigation of the catheter 100 to the treatment site, the outer and inner members 104, 106 may be in the first configuration, where the outer and inner members 104, 106 are movably disposed relative to each other. When the outer and inner members 104, 106 are in the first configuration, the tubular braid of filaments 110 may be movably disposed in the cavity 108 relative to at least one of the outer member 104 and the inner member 106. When the outer and inner members 104, 106 are in the first configuration, the catheter 100 may have a flexibility that is suitable for navigation through bodily cavities within the patient to the treatment site. After the distal end of the catheter 100 is positioned at the treatment site, the tubular braid of filaments 110 may be clamped between the outer member 104 and the inner member 106. The tubular braid of filaments 110 may be clamped by applying a vacuum to the cavity 108, which configures the outer and inner members 104, 106 in the second configuration. The vacuum may be applied through operation of the vacuum source 302 that is in fluid communication with and/or operably connected to the cavity 108. When the tubular braid of filaments 110 are clamped between the outer member 104 and the inner member 106, the position of the catheter 100 within the patient may have a flexibility that is less than the flexibility of the catheter 100 when the tubular braid of filaments 110 is not clamped between the outer and inner members 104, 106. In one example, the position of the catheter 100 within the patient may be locked or frozen or substantially locked or frozen. When the tubular braid of filaments 110 is clamped between the outer and inner members 104, 106, the catheter 100 may comprise a flexibility that is suitable for delivery of a medical device through the central lumen 116 of the inner member 104, or other lumens of the catheter 100.

After the tubular braid of filaments 110 is clamped between the outer and inner members 104, 106, the medical device may be delivered through the catheter 100, such as through the central lumen 116 or other lumens disposed around the central lumen 116, to the treatment site. The medical device may be inserted through a port or arm of the hub 112 that is in communication with the central lumen 116 or another lumen disposed around the central lumen 116. The medical device may be removed from the treatment site, and after the medical device is removed (i.e., by proximally retracting the medical device through the catheter 100), the vacuum may be removed from the cavity 108. The vacuum may be removed through operation of the vacuum source 302. When the vacuum is removed, the outer and inner members 104, 106 are configured in the first configuration and remove the clamp on the tubular braid of filaments 110. When the vacuum is removed, the catheter 100 may retain a flexibility that is suitable for retraction of the catheter 100 from the treatment site. After the clamp on the tubular braid of filaments 110 is removed, the catheter 100 may be retracted from the treatment site and removed from within the patient.

Various embodiments described herein can be used alone or in combination with one another. The foregoing detailed description has described only a few of the many possible implementations of the present invention. For this reason, this detailed description is intended by way of illustration, and not by way of limitation.

I claim:

1. A catheter comprising:
   an elongate tubular outer member;
   an elongate tubular inner member disposed within the outer member;
   an annular cavity disposed in between the outer member and the inner member; and
   a tubular braid of filaments disposed in the annular cavity;
   wherein the outer member and the inner member are movable relative to each other along intermediate portions thereof when in a first configuration and are not movable relative to each other when in a second configuration;
   wherein the tubular braid of filaments is movably disposed relative to at least one of the outer member and the inner member when the outer member and the inner member are in the first configuration; and
   wherein the tubular braid of filaments is fixedly disposed relative to both the outer member and the inner member when the outer member and the inner member are in the second configuration,
   and wherein the annular cavity is configured to be coupled to a vacuum source that applies a vacuum to the annular cavity such that when the vacuum is applied, the outer member and the inner member are drawn to each other to compress the annular cavity and clamp the tubular braid of filaments relative to the outer member and the inner member in the second configuration.

2. The catheter of claim 1, further comprising a port operably connected to the cavity for applying the vacuum.

3. The catheter of claim 2, further comprising a hub connected to proximal ends of the outer member and the inner member, wherein the port comprises a side arm of the hub.

4. The catheter of claim 1, wherein the tubular braid of filaments longitudinally extends over at least a portion of the inner member.

5. The catheter of claim 4, wherein the tubular braid of filaments extends in the cavity from a proximal end of the cavity to a distal end of the cavity.

6. The catheter of claim 1, wherein the tubular braid of filaments comprises a first tubular braid of filaments, wherein the catheter further comprises a second tubular braid of filaments, and wherein the first tubular braid of filaments longitudinally extends over a first portion of the inner member in the cavity and the second tubular braid of filaments longitudinally extends over a second portion of the inner member in the cavity.

7. The catheter of claim 1, further comprising a hermetic seal disposed at a proximal end of the cavity, and a hermetic seal disposed at a distal end of the cavity.

8. The catheter of claim 7, wherein the hermetical seal disposed at the proximal end of the cavity comprises a silicon diaphragm.

9. The catheter of claim 7, wherein the hermetic seal disposed at the distal end of the cavity comprises a connection of a distal end of the outer member and a distal end of the inner member.

10. The catheter of claim 7, wherein the tubular braid of filaments is fixedly attached to at least one of the hermetic seal disposed at the proximal end of the cavity and the inner member and the hermetic seal disposed at the distal end of the cavity.

11. The catheter of claim 1, wherein the tubular braid comprises an orientation that is approximately forty-five degrees from a longitudinal axis of the catheter.

12. The catheter of claim 1, wherein the tubular braid of filaments comprises sixteen filaments.

13. The catheter of claim 1, wherein the tubular braid of filaments comprises at least one of polyamide, elastomer, carbon fibers, metallic alloys, stainless steel, aramid fibers, polyethylene, and glass fibers.

14. A medical system comprising:
   a catheter comprising:
      an elongate tubular outer member;
      an elongate tubular inner member disposed within the outer member;
      an annular cavity disposed in between the outer member and the inner member; and
      a tubular braid of filaments disposed in the annular cavity, the tubular braid of filaments being at least partially movable relative to at least one of the inner member and the outer member; and
   a vacuum source in communication with the annular cavity, wherein the vacuum source is configured to apply a vacuum to the annular cavity to cause the elongate tubular outer member and the elongate tubular inner member to be drawn toward each other and clamp the tubular braid of filaments in order to prevent movement between the tubular braid of filaments and both the inner member and the outer member.

15. The medical system of claim 14, wherein the catheter further comprises a port operably connected to the cavity, wherein the port is connected to the vacuum source, and wherein the vacuum source is configured to apply the vacuum to the annular cavity by removing gaseous particles from within the cavity through the port.

16. The medical system of claim 15, wherein the catheter further comprises a hub in connection with proximal ends of the outer member and the inner member, and wherein the port comprises a side arm of the hub.

17. The medical system of claim 14, wherein the tubular braid of filaments longitudinally extends over at least a portion of the inner member.

18. The medical system of claim 17, wherein the tubular braid of filaments extends in the cavity from a proximal end of the cavity to a distal end of the cavity.

19. The medical system of claim 14, wherein the tubular braid of filaments comprises a first tubular braid of filaments, wherein the catheter further comprises a second tubular braid of filaments, and wherein the first tubular braid of filaments longitudinally extends over a first portion of the inner member in the cavity and the second tubular braid of filaments longitudinally extends over a second portion of the inner member in the cavity.

20. The medical system of claim 14, wherein the catheter further comprises a hermetic seal disposed at a proximal end of the cavity, and a hermetic seal disposed at a distal end of the cavity.

21. The catheter of claim 20, wherein the hermetical seal disposed at the proximal end of the cavity comprises a silicon diaphragm.

22. The catheter of claim 21, wherein the hermetic seal disposed at the distal end of the cavity comprises a connection of a distal end of the outer member and a distal end of the inner member.

23. The medical system of claim 22, wherein the tubular braid of filaments is fixedly attached to at least one of the hermetic seal at the proximal end of the cavity and the hermetic seal disposed at the distal end of the cavity.

24. The medical system of claim 14, wherein the tubular braid comprises an orientation that is approximately forty-five degrees from a longitudinal axis of the catheter.

25. The medical system of claim 14, wherein the tubular braid comprises sixteen filaments.

26. The medical system of claim 14, wherein the tubular braid of filaments comprises at least one of polyamide, elastomer, carbon fibers, metallic alloys, stainless steel, aramid fibers, polyethylene, and glass fibers.

27. The medical system of claim 14, wherein the vacuum source comprises a syringe.

* * * * *